(12) United States Patent
Farrow et al.

(10) Patent No.: US 8,529,483 B2
(45) Date of Patent: Sep. 10, 2013

(54) SHORT STRETCH THERAPEUTIC COMPRESSION DEVICE FOR THE EXTREMITY AND METHOD

(75) Inventors: Wade P. Farrow, College Station, TX (US); Barry L. Creighton, College Station, TX (US)

(73) Assignee: Farrow Medical Innovations Holdings LLC, Bryan, TX (US)

( * ) Notice: Subject to any disclaimer, the term of this patent is extended or adjusted under 35 U.S.C. 154(b) by 752 days.

(21) Appl. No.: 12/576,899

(22) Filed: Oct. 9, 2009

(65) Prior Publication Data

US 2011/0087145 A1    Apr. 14, 2011

(51) Int. Cl.
*A61F 5/00* (2006.01)
(52) U.S. Cl.
USPC .............. 602/21; 602/20; 602/60; 602/64
(58) Field of Classification Search
USPC ............ 602/20–22, 60–64, 5; D24/190–192
See application file for complete search history.

(56) References Cited

U.S. PATENT DOCUMENTS

| | | | |
|---|---|---|---|
| 1,227,700 A * | 5/1917 | Tucker | 602/21 |
| 2,687,723 A | 8/1954 | Stern | |
| 3,178,724 A * | 4/1965 | Perschke | 2/16 |
| 3,298,366 A | 1/1967 | Moore et al. | |
| 3,312,219 A | 4/1967 | Peckham | |
| 3,856,008 A | 12/1974 | Fowler et al. | |
| 4,172,456 A | 10/1979 | Zens | |
| 4,215,687 A | 8/1980 | Shaw | |
| 4,522,197 A | 6/1985 | Hasegawa | |
| 4,577,622 A | 3/1986 | Jennings | |
| 4,706,658 A | 11/1987 | Cronin | |
| 4,748,975 A * | 6/1988 | Yashima | 602/60 |
| 4,807,606 A | 2/1989 | Hasegawa et al. | |
| 4,809,684 A | 3/1989 | Gardner et al. | |
| 4,846,160 A | 7/1989 | Gardner et al. | |
| 5,033,119 A | 7/1991 | Wiggins | |
| 5,036,838 A | 8/1991 | Sherman | |
| 5,160,314 A * | 11/1992 | Peters | 602/21 |
| 5,218,954 A | 6/1993 | Bemmelen | |

(Continued)

FOREIGN PATENT DOCUMENTS

| | | |
|---|---|---|
| GB | 2373444 A | 9/2002 |
| WO | WO 99/36019 | 7/1999 |
| WO | WO 00/15139 | 3/2000 |

OTHER PUBLICATIONS

Patent Cooperation Treaty—Notification of Transmittal of the International Preliminary Report on Patentability, International Application No. PCT/US05/09483, Oct. 24, 2006, 9 pages.

(Continued)

*Primary Examiner* — Kim M Lewis
(74) *Attorney, Agent, or Firm* — Pate Peterson, PLLC; Warren M. Pate

(57) ABSTRACT

A compression device to be wrapped around the distal extremity of a patient for use in moderate to severe swelling/lymphedema. The device includes a flexible planar compression material of preferably short-stretch compression material. Fasteners are attached to the first and second band portions. The compression material in preferred embodiment contains short-stretch compression material with 20%-60% stretch. The device is designed such that it may be used to augment compression to the hand when used in conjunction with compression to the fingers and arm. The device is designed to be applied easier with one hand.

16 Claims, 12 Drawing Sheets

(56) References Cited

U.S. PATENT DOCUMENTS

| | | | |
|---|---|---|---|
| 5,333,605 A | | 8/1994 | Matsumura et al. |
| 5,350,418 A | * | 9/1994 | Janevski et al. ............... 602/21 |
| 5,387,183 A | | 2/1995 | Jones |
| 5,517,694 A | | 5/1996 | Fabry |
| 5,546,955 A | | 8/1996 | Wilk |
| 5,617,745 A | | 4/1997 | Della Corte et al. |
| 5,653,244 A | | 8/1997 | Shaw |
| 5,682,611 A | * | 11/1997 | Kline ............................. 2/160 |
| 5,897,518 A | | 4/1999 | Shaw |
| 5,918,602 A | | 7/1999 | Shaw et al. |
| 5,918,605 A | | 7/1999 | Real |
| 5,928,172 A | * | 7/1999 | Gaylord ........................ 602/21 |
| 5,939,339 A | | 8/1999 | Delmore et al. |
| 6,093,165 A | | 7/2000 | Estwanik |
| 6,109,267 A | | 8/2000 | Shaw et al. |
| 6,123,681 A | | 9/2000 | Brown, III |
| 6,254,554 B1 | | 7/2001 | Turtzo |
| 6,338,723 B1 | | 1/2002 | Carpenter et al. |
| D461,600 S | | 8/2002 | Domanski et al. |
| 6,536,051 B1 | | 3/2003 | Oh |
| 6,561,994 B1 | | 5/2003 | Mills et al. |
| 6,573,419 B2 | | 6/2003 | Naimer |
| 6,617,485 B2 | | 9/2003 | Herzberg |
| 6,694,523 B2 | | 2/2004 | Hurst |
| 6,790,192 B2 | | 9/2004 | Robinson |
| 6,805,681 B2 | | 10/2004 | Yokoyama |
| 6,860,862 B2 | | 3/2005 | Waldridge et al. |
| 6,977,113 B2 | | 12/2005 | Kody et al. |
| 7,135,007 B2 | | 11/2006 | Scott et al. |
| 7,276,039 B2 | * | 10/2007 | Garelick et al. ............... 602/21 |
| 7,364,556 B2 | | 4/2008 | Weaver |
| 7,442,177 B1 | | 10/2008 | Garelick et al. |
| 7,637,883 B2 | * | 12/2009 | Nyi ................................ 602/21 |
| 7,713,223 B2 | * | 5/2010 | Weber et al. .................. 602/21 |
| 2003/0149389 A1 | | 8/2003 | Daneshvar |
| 2004/0106889 A1 | * | 6/2004 | Robinson ....................... 602/64 |
| 2005/0192524 A1 | | 9/2005 | Lipshaw et al. |
| 2006/0010574 A1 | | 1/2006 | Linnane et al. |
| 2006/0161088 A1 | | 7/2006 | Voetsch |
| 2007/0010777 A1 | | 1/2007 | Dunshee et al. |
| 2007/0179421 A1 | * | 8/2007 | Farrow .......................... 602/75 |
| 2007/0276310 A1 | | 11/2007 | Lipshaw et al. |
| 2008/0104737 A1 | * | 5/2008 | Shepherd ........................ 2/20 |

OTHER PUBLICATIONS

European Patent Office Supplementary Partial European Search Report from European Patent Application No. 05731830.5 dated Apr. 8, 2008, 8 pages.

Patent Cooperation Treaty—European Patent Office, Notification of Transmittal of the International Search Report and the Written Opinion of the International Searching Authority, or the Declaration, International Application No. PCT/US2009/055051, Oct. 15, 2009, 11 pages.

Patent Cooperation Treaty International Search Report and Written Opinion of the International Searching Authority from Patent Cooperation Treaty Application No. PCT/US2005/09483, dated Jul. 6, 2005, 13 pages.

ASICS Mens Shooting Sleeve, www.amazon.com/exec/obdios/ASIN/FB000J40NYU/nextag-sg-20/ref-nosim, printed Feb. 1, 2007, 4 pages.

NBA Shooting Arm Sleeve, www.jumpusa.com/nba_shooting_sleeves.html, printed Feb. 1, 2007, 2 pages.

"Understanding compression therapy," Medical Education Partnership Ltd., 2003, 19 pages.

"3M™ Coban™ 2 Layer Compression System Commonly Asked Questions," 3M Copyright Feb. 13, 2007, pp. 1-3.

Press Release, "New 3M™ Coban™ 2 Layer Compression System Introduced for the Treatment of Edema Associated with Venous Leg Ulcers," May 1, 2006, 3 pages.

"3M™ Coban™ 2 Layer Compression System Patient Instructions," 3M Copyright 2006, 1 page.

Hawkins, J., "A new cohesive short-stretch bandage and its application," British Journal of Nursing, Jan. 2001, 4 pages.

Thomas, S., et al., "An Evaluation of a New Type of Compression Bandaging System," World Wide Wounds, Sep. 2003, 15 pages, www.worldwidewounds.com/2003/September/Thomas/New-Compression-Bandage.htm.

Lymphedema Can Happen to Anyone at Anytime at Any Age: Compression Sleeves: Arm Assist and Leg Assist BK & TH: Trinity Lymphedema Centers; Medop@aol.com: www.trinityic.org, 3 pages.

Medassist Orthotic Products, Ankle Foot Orthoses, Medassist Group, www.medassistgp.com, 6 pages.

http://fabrifoam.com//p-kneegard.html, retrieved on Sep. 30, 2005.
http://fabrifoam.com//p-anklegard.html retrieved on Sep. 30, 2005.
http://www.fabrifoam.com/p-achilleshealer.html retrieved on Sep. 30, 2005.
http://www.fabrifoam.com/p-psc.html retrieved on Sep. 30, 2005.
http://www.fabrifoam.com/p-prowrap.html retrieved on Sep. 30, 2005.
http://www.fabrifoam.com/p-superwrap.html retrieved on Sep. 30, 2005.
http://www.fabrifoam.com/p-anklewrap.html retrieved on Sep. 30, 2005.
http://www.fabrifoam.com/p-nustimwrap.html retrieved on Sep. 30, 2005.
http://www.fabrifoam.com/p-elbowgard.html retrieved on Jan. 7, 2010.
http://www.fabrifoam.com/p-pattstrap.html retrieved on Jan. 7, 2010.
http://www.fabrifoam.com/p-carpalgard.html retrieved on Jan. 7, 2010.
http://www.fabrifoam.com/p-mediwrap.html retrieved on Jan. 7, 2010.
http://www.fabrifoam.com/p-wristwrap.html retrieved on Jan. 7, 2010.

"Use of a Velcro Wrap System in The Management of Lower Limb Lymphoedema/Chronic Oedema," Journal of Lymphoedema, 2008, vol. 3 No. 2, pp. 65-70.

* cited by examiner

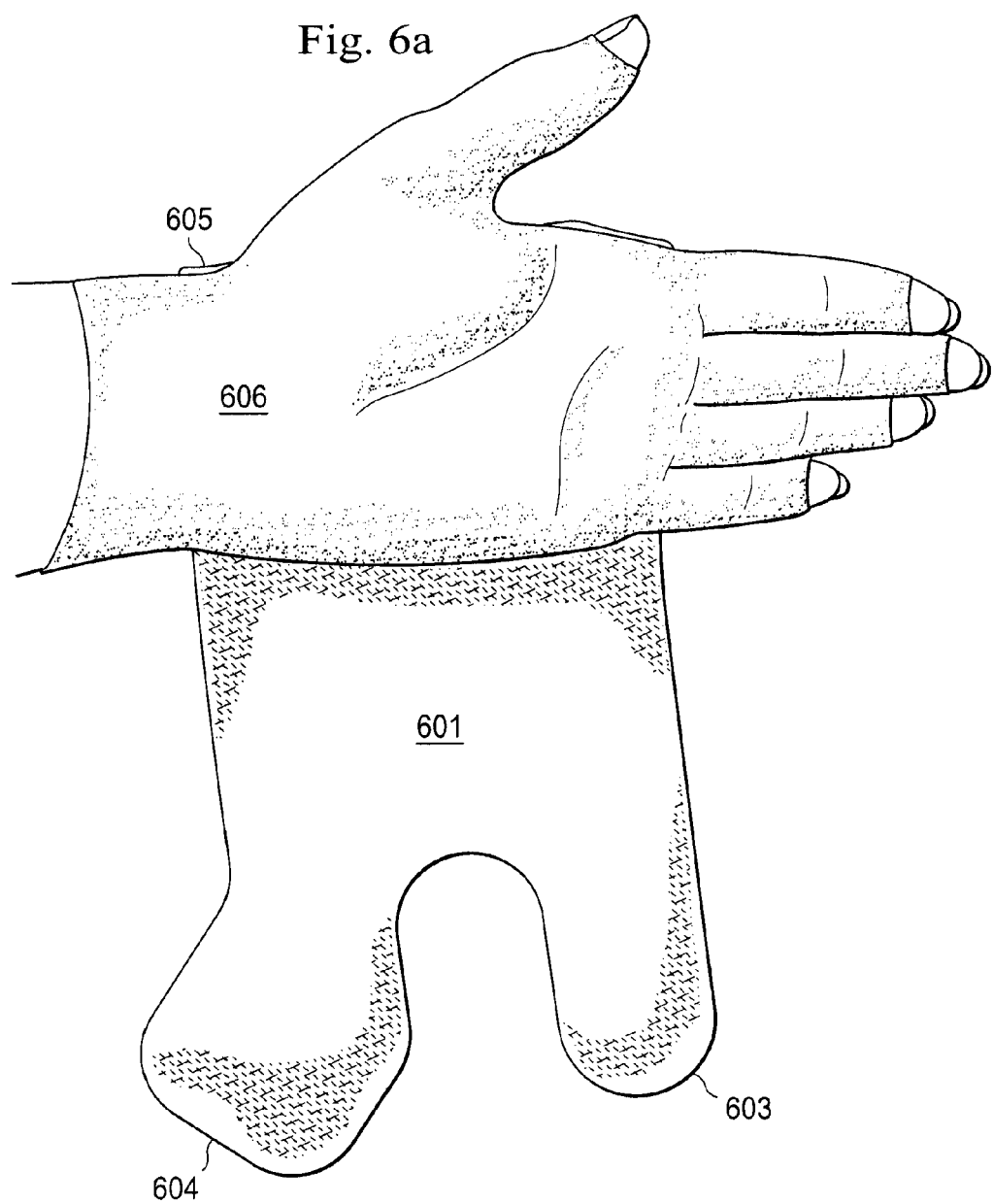

SHORT STRETCH THERAPEUTIC COMPRESSION DEVICE FOR THE EXTREMITY AND METHOD

The field of the invention is wrist/hand and foot compression devices. Specifically, the invention relates to a compression device to apply therapeutic compression to the wrist and hand or to the foot, using a unique planar design and hybrid compression device consisting of part compression gauntlet and part glove or toecap/anklet configuration. Trim to fit components, markings, and unique materials make ambidextrous use and sizing easier for the patient.

BACKGROUND OF THE INVENTION

There are a wide range of products designed to provide therapeutic compression to the hand and wrist areas. These products range from simple elastic bandages to complicated electromechanical devices. Depending on the need of the patient, higher levels of compression may be needed on the hand and wrist areas. Such devices are commonly used to treat lymphedema of the hand and other maladies. Typically, compression is needed on the arm, wrist, and hand. Some patients have swelling of the fingers and garments typically stop at the base of the fingers, at the proximal interphalangeal joint (PIP), or the distal interphalangeal joints (DIP). These garments for the hand are classified as compression gauntlets, ½ finger compression gloves, and full finger compression gloves. These garments come in a wide range of compression levels, and sizes, such that many garments are needed to fit the range of different degrees and anatomical locations of swelling correctly. There remains a need for a single garment to address a full range of patients, as well as a garment which can provide very high compression levels to the dorsal hand to reduce edemas and reverse tissue fibrosis, while not overly constricting the hand movement and manual dexterity.

Additionally, due to fluctuations in hand and wrist size due to swelling, as well as need for Durable Medical Equipment (DME) clinics and hospitals to reduce inventory, ability to trim the compression device to fit a wide range of patient hand and wrist sizes and wide range of patients with different degrees and extent of swelling is needed.

SUMMARY OF THE INVENTION

The present disclosure is directed to a hand and wrist compression device to the hand, which can be used in conjunction with a compression glove. In some embodiments, the current invention merges the compression glove into a new class of hybrid compression garment which has short-stretch compression to the dorsal and palmar hand, but four way stretch to the fingers and thumb, and allow trimmability as needed by the patient. This garment may be worn with a compression sleeve, or incorporated into a full length arm and hand garment as one piece.

In some embodiments, the current invention creates a bidirectional garment which can be applied to either the right or left hand, such that the garment can be used ambidextrously. This is accomplished by using unbroken loop (UBL) compression fabric or similar hook compatible compression material on both inside and outside of the garment, such that its direction can be easily reversed. The fabric can be laminated with thin breathable foam or thin polyurethane layer, or other lamination technology, as is known in the art.

In some embodiments, the invention is directed to a compression hybrid glove which is part glove and part compression gauntlet. This allows maximal edema control on the dorsal and palmar hand, but maximizes finger comfort and range of motion by utilizing thin compression fabric material on the finger and interdigit areas such as the webbing between fingers.

In some embodiments, the current invention provides a planar compression device designed to be used in conjunction with an underlying compression anklet, compression toe cap, or stocking.

In some embodiments, the current invention provides a hybrid compression device which incorporates a stocking, anklet, toe cap, or compression toecots with a short-stretch or nonelastic planar compression material, in order to better control severe swelling of the dorsal foot, such as for patients with moderate to severe lymphedema, among other maladies.

DETAILED DESCRIPTION OF THE PREFERRED EMBODIMENTS

Figure 1:
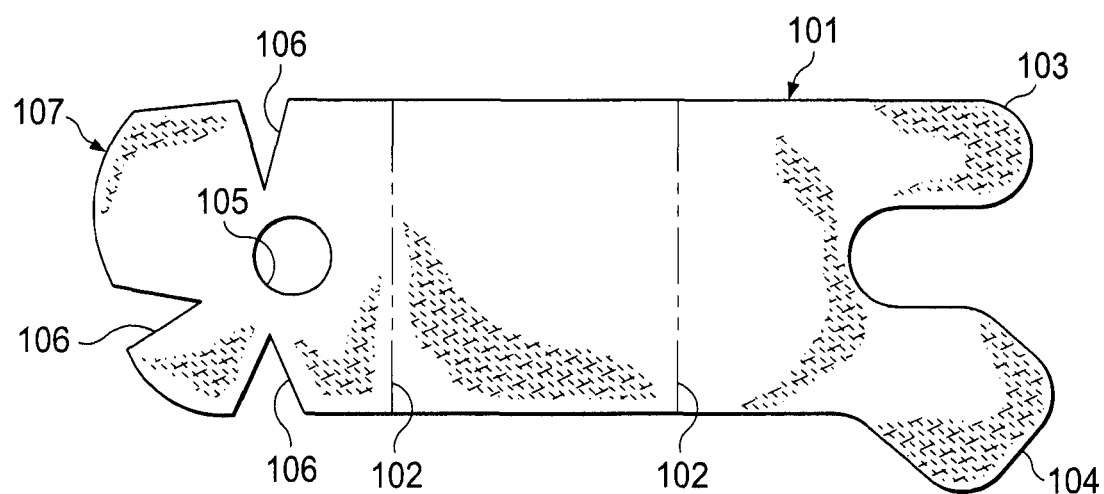
FIG. 1 is a drawing of a preferred embodiment of a hand compression gauntlet.

Lymphedema and other conditions that cause swelling can affect the upper extremity. The locations and severity of the swelling differ between patients and conditions. In some patients, this affects the lower arm. In others, this affects the hand only. In the majority of cases, the swelling is worse the more dependent the location of the limb, such that the more distal on the extremity, the worse the swelling. Additionally, involvement of the fingers varies widely. In severe cases, compression is needed on the hand, wrist, and on each finger out to the distal interphalyngeal (DIP) region of each digit. In other patients, the swelling only extends to the proximal interphalyngeal (PIP) region of each digit. In other patients, the swelling is mostly in the hand dorsally and stops at the base of the fingers. Therefore, a wide range of solutions are needed. Compression gloves are known in the art. Medical grade compression ranges typically start around 15 mm Hg and go up to 50 mm Hg. Most mild lymphedema patients with hand swelling require compression in the 20-30 mm Hg range, or for more severe lymphedema in the 30-40 mm Hg range. Currently, flat knit compression glove technology is utilized for higher compression levels for moderate to severe lymphedema. Microfine type material has already been commercialized for a light compression glove in the 20-35 mm Hg range and is trimmable and for mild to moderate lymphedema and is available internationally (Haddenham Health in the UK and Farrow Medical in the US). It is understood exact compression ranges commonly used differ by country, as there are many compression standards (US has no formal standard but compression ranges typically are 8-15 mm, 15-20 mm, 20-30 mm, and 30-40 mm Hg ranges). France has their own standard, as does Germany and the UK. The German Raul standard is very popular, and uses compression ranges of 18-21 mm (Class I), 23-32 mm (class II), 34-46 mm (class III), and >49 mm Hg (class IV).

Exact definitions of compression classes vary. Similarly, exact definitions of compression materials vary. Extensibility less than 15-20% is generally considered non-elastic. Compression levels 20%-70% are generally considered short-stretch, although definitions may range from 15% to as high as 100% extensibility. Foeldi's Textbook of Lymphedema advocates. Moderate stretch compression garments range from upper limit of short-stretch to 140%. In Foeldi's text, he considers long stretch compression garments are considered ones with extensibility greater than 140%.

The current invention discloses a short-stretch compression device which can be applied to the hand area. In some embodiments, this compression device is a gauntlet which is applied over or instead of a compression glove. In other embodiments, this device is a hybrid device consisting of a short-stretch compression gauntlet to the hand area, with built in compression to apply to each affected finger as well as the thumb. The device is designed to conform to the hand and thenar eminance areas, and to provide consistent compression to the back of the hand area even during movement. In some embodiments, the garment may have nonelastic or medium or long stretch compression materials.

To achieve this, the garment can be constructed in different ways. To allow the garment to be used ambidextrously, in some embodiments it is constructed with hook compatible material on both sides using thin lamination or thin foam technology or sewing/serging to adhere the layers together. This way the garment can be utilized for either the right or the left hand. This is advantageous as a medical clinic or company stocking the garment requires less inventory to be stocked to fit a wide range of patients. The garment may additionally have a pocket on the inside of the dorsal aspect of the hand, to allow the insertion of padding such as spacer fabric or foam. The foam may be 0.2 cm-1 cm thick and may consist of flat foam or shaped foam in order to facilitate lymphatic flow out of the hand. The shaped foam in some embodiments may consist of channels to provide high compression areas to push edematous fluid out and low compression areas to channel lymphatic flow of fluid and facilitate its return proximally. In other embodiments, spacer fabric is chosen for its light weight and superior breathability.

The garment preferentially consists of a short-stretch material. Short-stretch material with a compression range of 15-100% maximal extensibility is desired, with the preferred embodiment laying in the 30-60% range, but may also consist of inelastic or medium to long stretch fabrics for any of these embodiments. Extensibility refers to the increase in length or width of a material when it is stretched, as well as its capacity to return to its normal or prestretched shape and size when released. For those known in the art, the extensibility of a material is often referred to as the elasticity of the material. The purpose of short-stretch compression is that the product can be applied at or near maximal stretch. In addition, short-stretch compression materials can be engineered to have a more abrupt end of stretch, wherein the garment material locks out and does not stretch further. The garment abruptly approaches its stretch limit and does not easily stretch much further. This end-stretch or garment lock-out is considered the maximum extensibility of the material. This is referred to as bandage "lock out". The garment lock out is considered the maximal stretch or maximal extensibility of the compression material in the case of short-stretch compression garments. The garment lock out gives the user a distinct tactile feedback, so that the user can feel or know when the garment is at or near its maximal stretch. By designing a compression material with distinct band or garment lockout, it is possible that a predetermined baseline compression level can be easily calculated based on circumference. Thus, a hand compression gauntlet can be engineered where the garment is applied at or near end stretch with a highly repeatable and reliable baseline compression level. The use of short-stretch is quite unique in that it allows a band type design with Velcro® hook and look to be used which can provide a precise level of compression which otherwise might require a custom compression garment.

Additionally, for movement of the limb component or muscles underlying the garment, the muscles expand and press against the garment. This results in higher subgarment compression levels against the skin. Since the skin contains a large amount of superficial lymphatics, including many lymphangion micropumps which facilitate the return of lymph fluid, a short-stretch compression material applied over a muscle can better stimulate venous and lymphatic return than a more elastic material with a poorly defined lock out.

Nonelastic compression materials also augment the venous and lymphatic action of the muscle pump, but have potential drawbacks. One drawback is that there is little stretch so it is difficult to determine the baseline or resting compression when applying the product. The baseline or resting compression level is the compression when the garment is applied to a limb in the resting or supine state. Changes in limb position relative to the heart, or activation of muscles underlying the compression material, can affect the baseline or resting compression level. Additionally, nonelastic compression materials do not always conform to the limb. Many experts feel short-stretch compression has better limb conformability, better reliability and predictability for the user to apply the garment with predictive resting compression level, but still have the same degree of activation of the venous and lymphatic muscle pumps due to the bandage lockout.

Garment lock out may be achieved by utilizing a woven material, meaning there are at least two systems of threads (warp and weft threads) at right angles to each other. By contrast, typical compression stocking material is designed by forming looped stitches. Using yarns which are twisted with cotton over spandex or polyamide threads combined with a twisted cotton crepe yarn is one way to achieve bandage lock out for such garments. Cotton spun around the elastic filaments improves skin tolerance and allows maximum extension of the bandage. Woven, knitted, or non-woven elastomeric materials such as weftlock, powernet, techsheen, lockstitch, superlock, triskin, stretch satin, gentislismo, or tricot may be utilized to make compression material for the garment disclosed. Knitted compression fabrics can be engineered to provide desired short-stretch type function. Thin film coatings or flame lamination or thin foam lamination techniques, among other methods known in the art, can be utilized to combine materials to get the desired compression and short-stretch function. Woven and knitted or various knitted fabrics can also be utilized. By changing the angle the material is cut, this can change the baseline compression and extensibility and also affect the extent of garment lock out at or near end-stretch.

FIG. 1 shows one preferred embodiment of such a compression device 101. The compression material 101 may be one of any constructions described above, but is preferably a Velcro® loop type compression fabric which is laminated with thin polyurethane type lamination or flame lamination technique or other techniques as are known in the art. The fabric may be cut at some angle relative to the warp direction for all the garments in order to achieve the most consistent abrupt end-stretch, while creating baseline predetermined resting compression levels when applied at or near end-stretch which are in a safe range for the patient and within therapeutic range (15 mm-50 mm Hg). By altering materials or angle at which fabric(s) are cut, short-stretch compression with abrupt end-stretch and multiple predetermined resting compression levels can be achieved. 103 details a band, which is part of the garment. This band is designed to go around from the lateral (ulnar) side of the hand and over the dorsum of the hand. Velcro® type material is applied from the edge of the band onto the fabric to hold the gauntlet in place, or is sewn onto the end of the band or under the band, such that it is not visible.

Band 104 details a unique band which has diamond configuration. When this band is pulled over the dorsum of the hand, it creates a vector force that not only pulls across on the band, but pulls down toward the wrist. This becomes important with hand movement like wrist dorsiflexion, where the vector forces of this band prevent the compression fabric on the back of the hand from loosening or buckling. Other embodiments of the band 104 are possible, such as a Y shaped band or T shaped band, in order to create correct vector forces and help garment to better conform to the shape of the underlying limb portion.

105 details a thumb hole, and options cuts 106 are utilized in the preferred embodiment and then the fabric refastened or resewn together in order to make the flap to the left or right of the thumb hole better conform to the anatomy of the palm, where the thenar eminence is located. The curve of the material 107 is also cut in order for the garment to better conform to the base of the palm in a shape similar to the outline of the base of the thenar eminence. Dotted lines 102 show where optional underlying foam pad would be attached.

Figure 2:
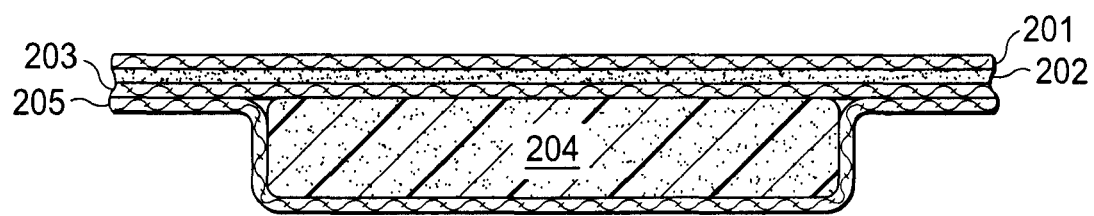
FIG. 2 is a drawing of a cross section of a hand compression gauntlet.

FIG. 2 shows a cross section of the materials and is shown proportionally and to line up with FIG. 1. 201 represents one layer of compression material and 203 represents a second layer of compression material. 202 represents the optional lamination material of thin polyurethane, thin foam, or other laminating substances as are known in the art. Together 201, 202, and 203 represent the cross section of material 101.

The material 204 represents an optional padded area which may be high quality dense foam which may be 0.2 cm-1 cm thick and located under the compression garment with optional third material 205 to hold the padding 204 in place. The foam may be channeled, waffled, or flat foam, and foams of different densities can also be used. Dense foam is sometimes better at softening and reducing fibrotic areas due to lipodermatosclerotic process as seen in lymphedema. Softer foam might be better over knuckle areas or the reduce subgarment pressure on the knuckles, providing more uniform compression in order to reduce and maintain edema reductions. In some embodiments, several pieces of foam will be sent together with the garment in a kit form, and the patient can select which to use, or use thicker foam initially to reduce the swelling, and then switch to thinner foam for a lower profile for long term use. The patient can selectively remove the foam layer 204 as desired. In other embodiments, the layer 204 represents a spacer fabric. Spacer fabric provides good padding and excellent breathability, consisting of two layers of material with monofilaments or other materials which span between the layers to provide spacing and compressibility. The type and thickness of the chosen spacer fabric may depend on the severity of the swelling of the patient. In some embodiments, the spacer fabric may have channeling built into it to facilitate areas of high compression and lower areas of compression to facilitate lymphatic flow back up the limb.

In some embodiments, the foam would be used but the third material 205 would not be utilized. Instead, the foam would have a cloth covering laminated or no covering and the sponge would be against the skin. In the case of some spacer fabrics, no fabric is needed and the spacer fabric has smooth surface against the skin. In either of these situations, Velcro® type hook and look may be used to hold the padding in place. In the case of some spacer fabrics, the spacer fabric has soft hook compatible surface which would work nicely to hold padding in place on the underside of the garment in a location where it provided adequate padding to the dorsal hand area.

In other embodiments, thick foam or other padding material such as spacer fabric 0.2 cm-1 cm thick would be inserted into the garment such that the back of dorsal hand had additional padding. Some spacer fabrics have compression and stretch and it is possible to use one or more layers of spacer fabric to make the whole garment 101 and there would only be spacer fabric and no lamination or other compression materials needed. In other embodiments, the spacer fabric would go on the whole underside of the garment and a compression fabric or UBL compatible compression material would be laminated, sewn, or ultrasonically welded or otherwise attached to the outer layer of the garment.

Figure 3:
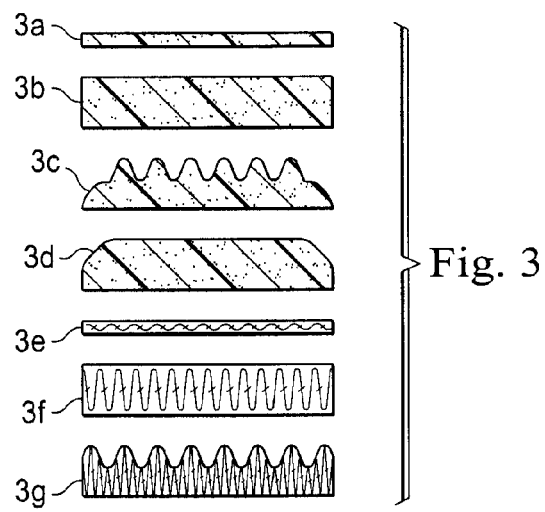
FIG. 3 is an illustration of multiple paddings which may be used in conjunction with a compression device.

FIG. 3 shows different embodiments of padded material. 3a represents thin foam preferably 4 mm thick but as thin as 2 mm thick. 3b represents thicker foam preferably 8 mm thick but up to 1.0 cm thick. 3c represents a channeled piece of foam which may have thickness 0.2 cm-1 cm thick. 3d represents foam with beveled edges which is desirable in thicker foam in order to allow proper compression gradients and comfort at the edges of areas 102 of FIG. 1. In the case of 3d, the wider edge would go against material 203 and the more narrow beveled edge would go against material 205. Material 205 can be laminated to the padding layer, if present or may be absent in some embodiments of the current invention, which would reduce production costs.

FIGS. 3e to 3g show spacer fabric embodiments of the current invention. In FIG. 3e, the spacer fabric has two layers of fabric with monofilament or similar technology to provide compression resistance and very high breathability of the material. Use of spacer fabric for such a garment can provide superior breathability and decrease moisture build up next to the skin. Moisture buildup can lead to higher risk of fungal infection and secondary development of fungal dermatitis as well as cellulitis so this breathability is very advantageous—and why the author does not prefer to use neoprene type compression materials or even Breathoprene®, which has only limited breathability. These materials are subideal for lymphedema patients, who are at higher risk of infection and complications and require long term daily compression and in many cases require this compression day and night.

FIG. 3e shows a thin spacer fabric and FIG. 3f shows a thicker spacer fabric. FIG. 3g shows a spacer fabric with linear channels in the spacer fabric. Other embodiments such as waffled foam or spacer fabrics or wavy linear channels are also possible. The density and thickness of the foam as well as the surface is chosen to provide adequate padding and compression for maximizing comfort, edema control, and in the case of lymphedema, to reduce lipodermatofibrotic areas by using compression and padding over time.

Figure 4A:
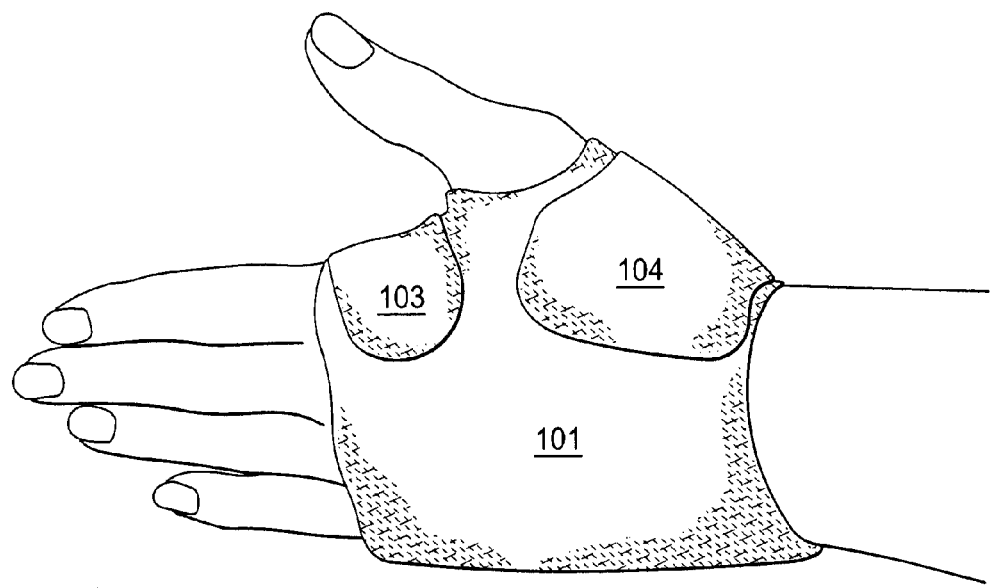
FIGS. 4a and 4b are illustrations of the dorsal hand with a compression gauntlet applied.
Figure 4B:
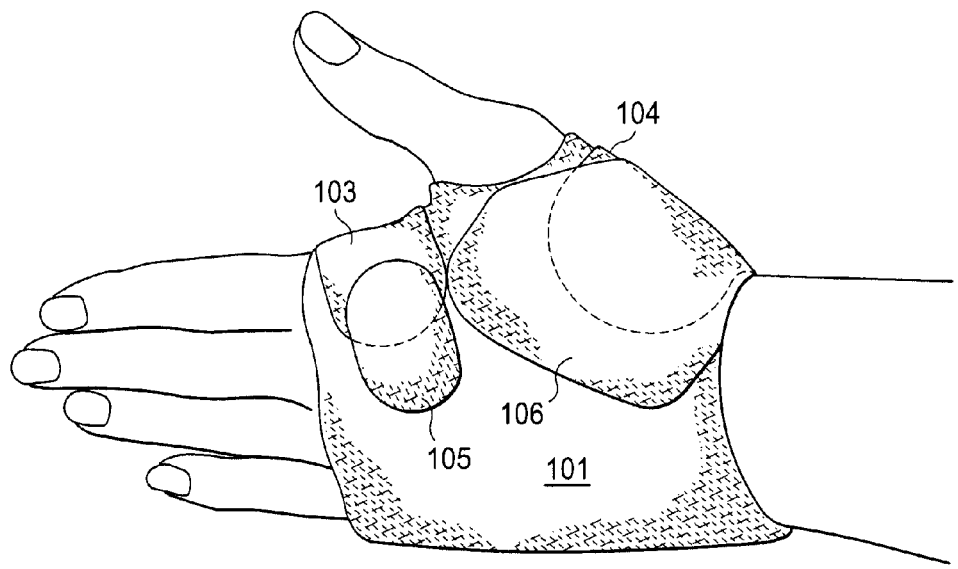

FIG. 4a shows the dorsal view of the hand with the garment of FIG. 1 applied. Note how the band pulls across and down and has a vector summation very similar to the perpendicular course of the skin between the base of the thumb and the wrist laterally. This polygonally shaped band provides more consistent application of compression and improves ability of patient to move wrist freely while maintaining therapeutic compression throughout the range of motion. FIG. 4b shows the garment with separate Velcro® like hook compatible pieces 105 and 106 applied to the bands 103 and 104 and underlying dorsal portion of the garment 101. The size and shape of the Velcro can be altered to help create the correct vector summation to provide consistent and comfortable compression through the normal range of motion of the hand and wrist. The Velcro® type hook material can be modified by the manufacturer or end user to other shapes as needed in order to provide correct vector forces on the garment 101 and provide comfortable predetermined resting levels of compression.

Figure 5:
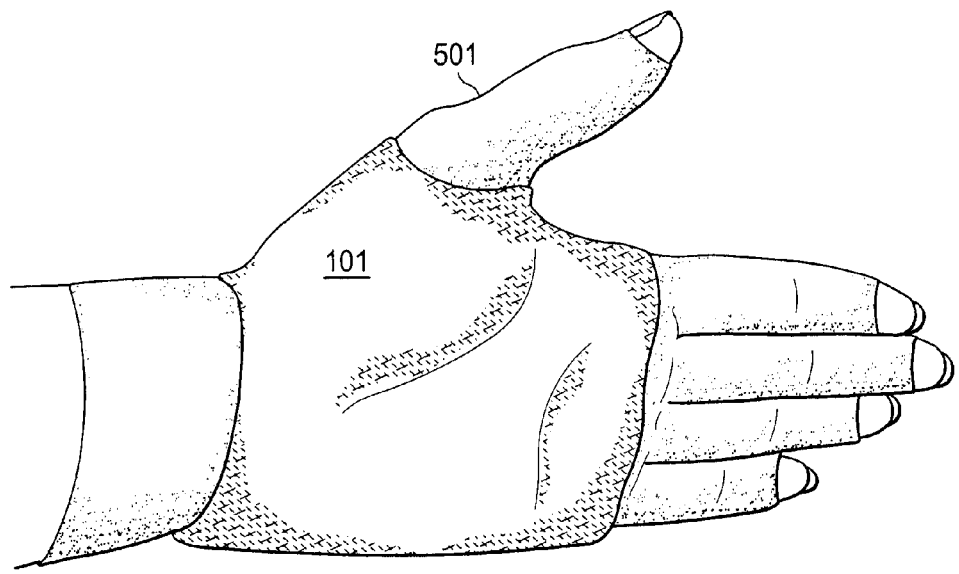
FIG. 5 is an illustration of the palmar hand with a compression gauntlet applied over a glove.

FIG. 5 shows the palmar surface of compression garment 101 applied over a thin compression glove 501. This compression glove may be made of microfine compression material which is trimmable, may be flat knit compression material, or other compression material as is known in the art. The compression glove in some embodiments comes with the kit of foam and compression hand gauntlet 101, and may be trimmable. Utilizing the garments together, comfortable compression with higher therapeutic compression on the dorsal hand is possible than utilizing any compression glove alone. Because the garment 101 is designed with nonelastic or short-stretch elastic material, it provides high level of therapeutic compression, while the thin compression material of the glove 501 provides maximum flexibility and movement of the fingers, with minimal material to the finger webbing at the base of the fingers. Please note that compression material 501 can be identical to compression material 606 used in other illustrations described below.

FIG. 6a shows an illustration of one embodiment of a hybrid compression garment for the hand and wrist. This garment has planar compression material 601, band 603, diamond shaped polygonal band 604. The garment also is comprised of compression material 606 to the fingers in a glove-like configuration. This garment is permanently attached along the thumb side (radial side) of the garment 605. In some embodiments, the thumb area of edge 605 is not sewn such that the thumb compression material can be pushed through a hole in the material 601, allowing the thumb to exit on either side. This is important such that the garment may be used on either the right or left hand. In other embodiments, there is no thumb hole and the material 605 is permanently or cooperatively attached to glove section 606. The glove section 606 may be microfine or trimmable compression material, or may consist of compression fingercots are attached to each other and/or the material 601, such that compression can be applied to each digit, as well as to the dorsal and planar aspect of the hand.

Figure 6B:
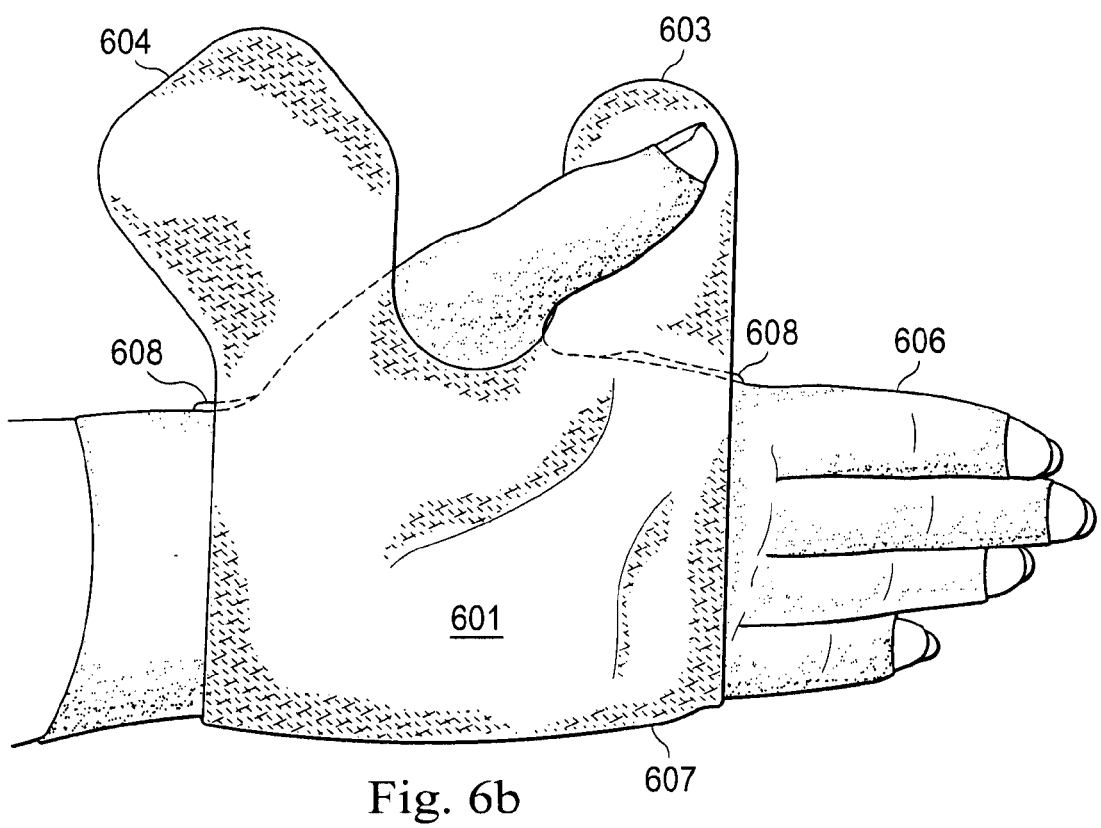
FIGS. 6a, b, c, and d show illustrations of hybrid compression garments.
FIGS. 6e, f and g show illustrations of an embodiment of the current invention modified for application to the foot.
FIG. 6h illustrates the foot of a patient with a chronic dorsal hump for severe chronic lymphedema.

FIG. 6b shows another embodiment of a hybrid garment. In this garment, there is a partial glove involving the fingers and the interwebbing between each digit. The planar compression material 601 is preferably sewn or permanently attached to the both the palmar and dorsal sides of the finger compression material 606. The compression material 606 does not need to be an entire glove, but in some embodiments it is a whole glove. In other embodiments, the finger sections are all interconnected and then at the level just proximal to the finger webbing, the material 606 is sewn to the compression material 601 on the dorsal side. The material 601 continues around the ulnar side of the hand 607 and wraps back around to the opposite side 608. At side 608 the material may be anchored around the thumb with overlap, or may have microfine or similar compression material as used on fingercot compression material 606. The band 603 and polygonally shaped band 604 then wrap around to the dorsal side of the hand where they are anchored.

Use of short-stretch type material for planar compression material 601 allows for more therapeutic compression on the hand area, which is often problematic for lymphedema patients. The use of more 4-way stretch compression material for 606 is important for finger manual dexterity and maximum comfort. The hybrid garment is therefore in this invention more effective at swelling control, while maximizing comfort, manual dexterity, and low profile to the user. The resultant garment is low profile but very compressive if needed, while allowing more breathability and finer manual movements than flat knit style compression gloves, as are known in the art.

Figure 6C:
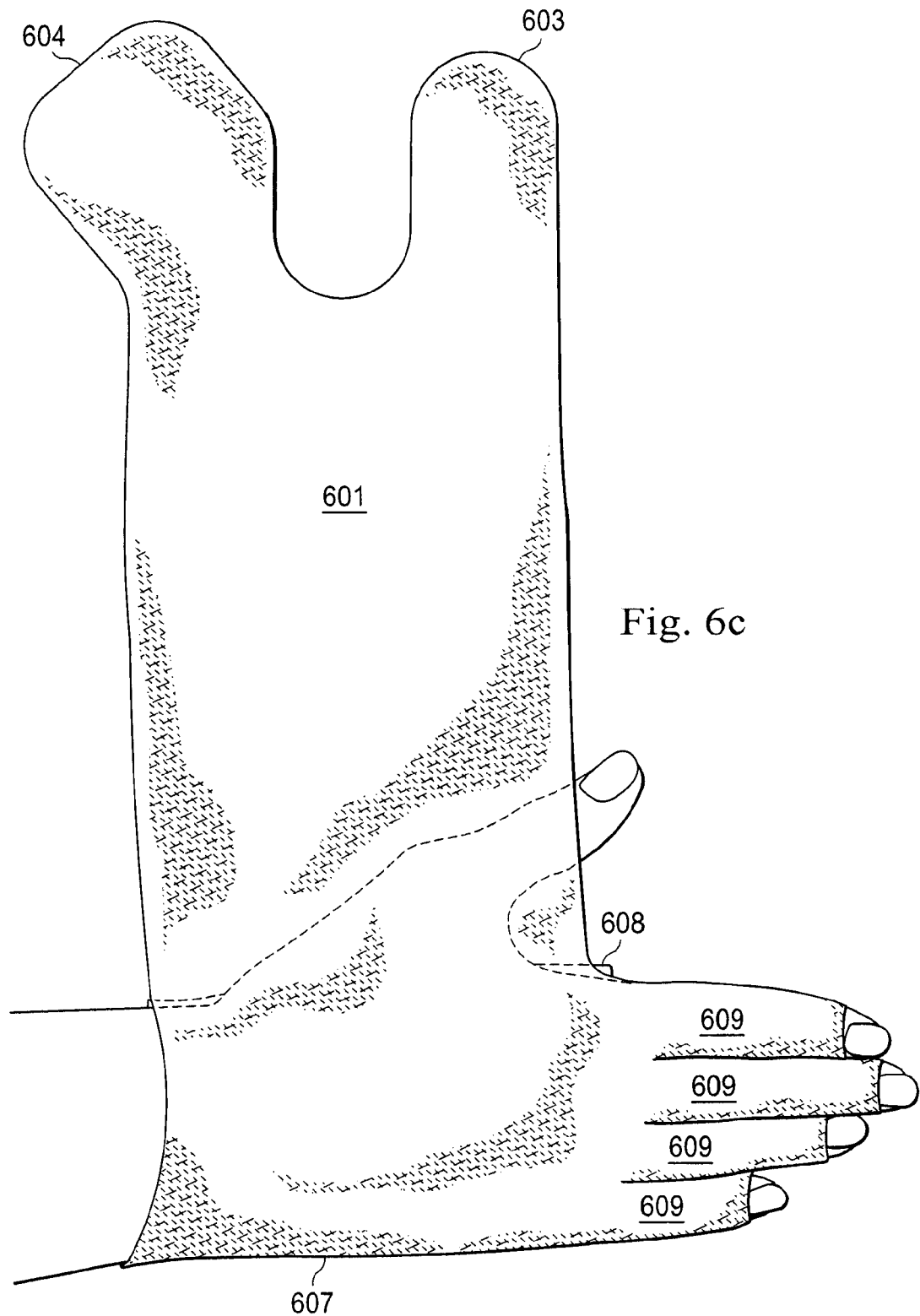

FIG. 6c shows another illustration of a hybrid compression garment, which is a hybrid compression gauntlet glove. This compression garment very similar to garment 6B, but different in that the compression fabric to the fingers 609 is the same material and is contiguous with the planar compression material 601 as a single sheet. The sides of the digits and finger webbing contain compression material 606, which is illustrated in this drawing. The dorsal and/or plantar aspects of the digits are made with the same compression material as 601. This material thus gives more integrated look and can provide short-stretch type compression to the fingers.

Figure 6D:
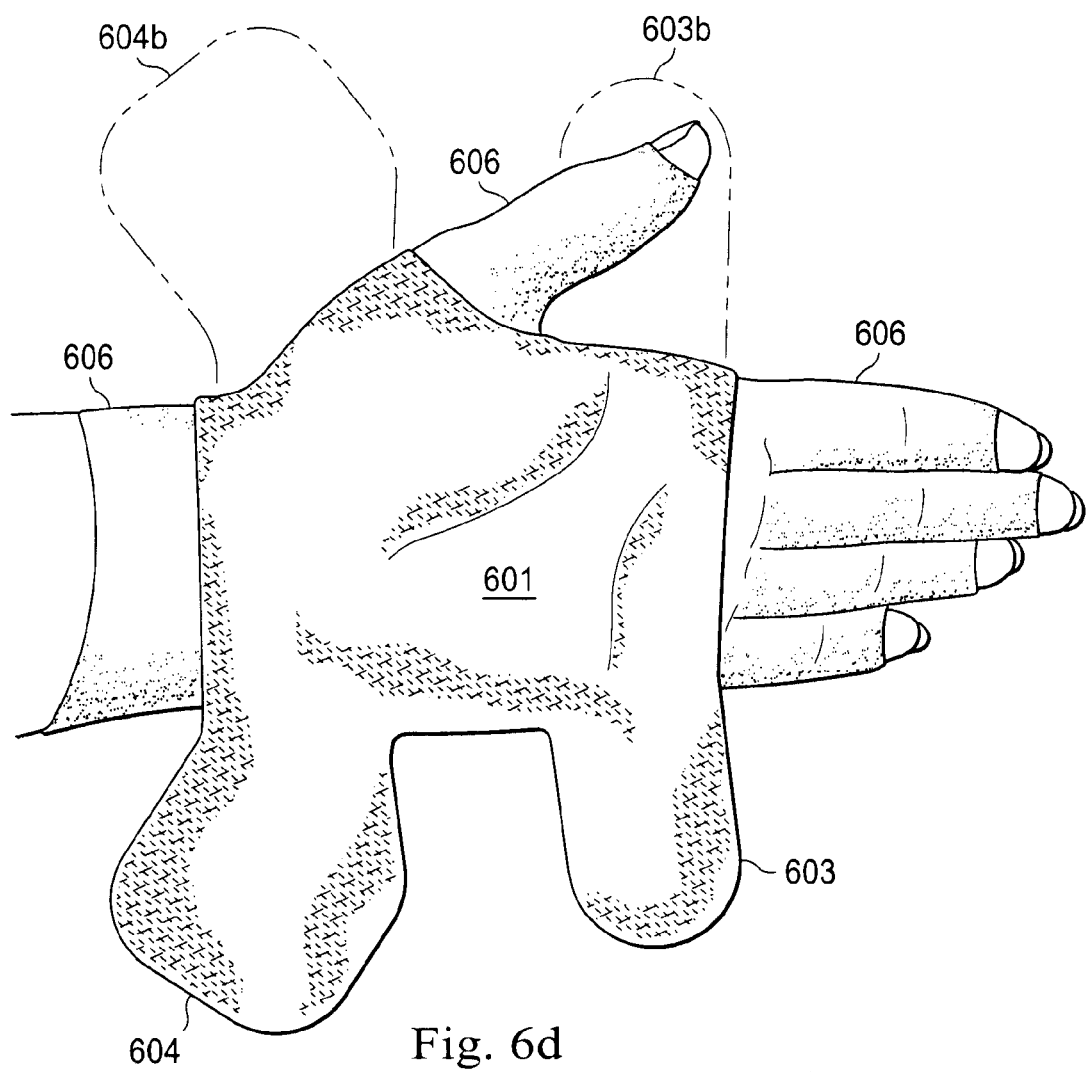

FIG. 6d shows another embodiment of a hybrid compression garment. This hybrid garment is a compression gauntlet glove with optional compression sleeve. This garment has four way stretch compression material 606 which might be microfine compression material, circular knit construction, flat knit compression material, or other compression gloves as known in the art. The area 601 comprises the planar compression material which is short-stretch or nonelastic compression material, preferably laminated compression fabric with outer UBL type material, although other materials are possible. This illustration shows the palmar side of the hand facing up. The bands 603 and polygonal band 604 are permanently attached or preferably cut from a singular piece of compression material 601. In some embodiments, the radial side of the compression material (near the thumb) will be continuous to the back (dorsum) of the hand, creating a C-clamp type compression on the hand. In these embodiments, only two bands are necessary. Compression material 606 would in some embodiments be attached between the ulnar side of compression material 601, closing the open end of the C-clamp. This makes donning easier, then the bands would provide the increased compression to the hand area. In other embodiments, there would be two separate sections of compression material 601. One would be on the dorsal side of the hand and one would be on the palmar side of the hand. In this configuration, preferably compression material 606 would be sewn on both the ulnar and radial sides of the hands to connect the compression material 601. Since compression material 606 has more stretch, this would make donning easier. In the case of separate compression material, additional bands 603b and 604b would be needed to apply tight therapeutic compression to the hand area. Compression material 606 in this case may stop or may extend all the way up the arm, forming a compression sleeve. The compression glove and sleeve may be circular knit, flat-knit, or sewn from four way stretch compression material, as known in the art. The short-stretch or nonelastic compression materials 601 provide tight therapeutic compression to the hand for cases of severe swelling, such as moderate to severe lymphedema.

Figure 6E:
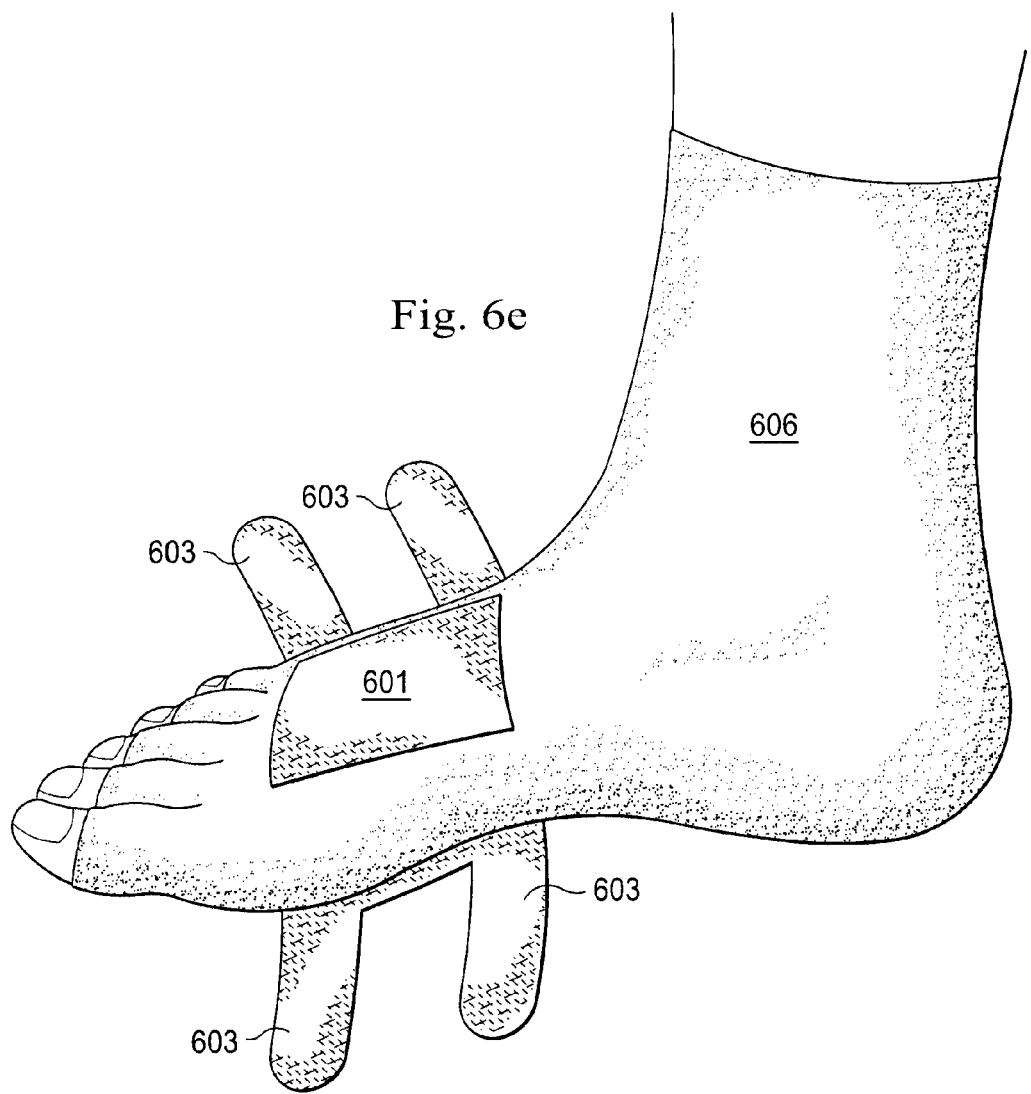
Figure 6F:
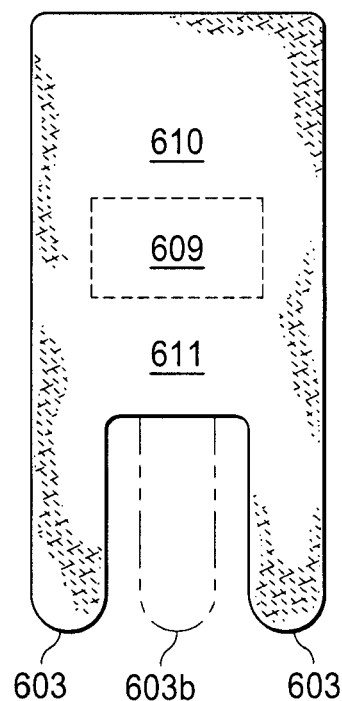
Figure 6G:
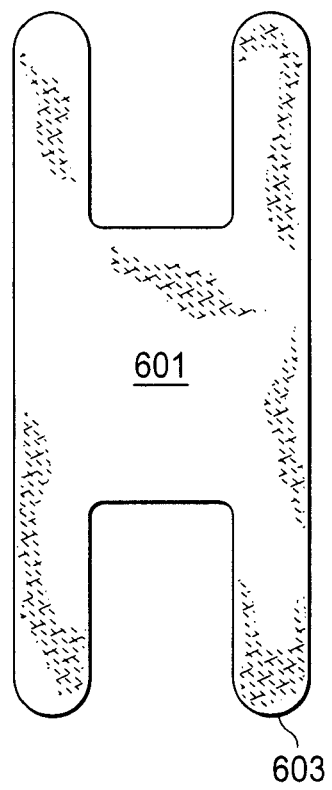

FIGS. 6e, 6f, and 6g show a hybrid compression garment designed for a foot. In the case of lymphedema, there is often lymphostatic pooling on the dorsal foot, resulting in a dorsal hump of high protein fluid. This swelling can be very severe in chronic lymphedema cases. It is difficult to increase compression in the midfoot, due to risk of increased pressure to the metatarsal heads medially on the great toe, and laterally on the 5th toe. Therefore, these severe patients often bandage long term with lymphedema bandaging, which is time consuming and difficult to self apply. This dorsal foot lymphedema is difficult to control without short-stretch type compression, and even courses of Manual Lymph Drainage with Complete Decongestive Therapy often does not adequately reduce/control the lymphedema. Hence, additional compression is needed for moderate to severe lymphedema patients in addition to or instead of their normal compression garments.

Additionally, on some days patients may need additional compression to these areas and on other days they do not. FIG. 6E shows a hybrid compression garment applied to a foot area. Compression material 606 may be a closed toe compression stocking, a compression anklet, or preferably microfine four way stretch compression material including trimmable toe caps. In this embodiment, short-stretch or non-elastic compression material is preferably chosen. In this illustration 6e, the compression material 601 is cooperatively attached or permanently attached to compression material 606 on the dorsal foot. On the plantar aspect of the foot is another section of compression material which preferably comprises most or all of the bottom of the foot between the compression bands 603. In this drawing, the compression bands make an H configuration in relation to the compression material. FIG. 6G shows the plantar compression material and H shaped bands in more detail. Turning back to FIG. 6E, the compression material 606 is preferably on the sides of the foot due to higher extensibility. This plantar compression material may be cooperatively or permanently attached, or may be a separate piece of compression material, and used only at times while patient's edema/lymphedema is exacerbated. It is possible to reverse these planar compression material and put the H bands on the dorsal foot, but this is probably not advisable unless extremely thin material used for the bands, due to risk of constant pressure and discomfort from walking on the bands all day when they are affixed to the plantar foot.

FIG. 6f shows a single planar piece of compression material that can be utilized to control dorsal foot moderate to severe lymphedema. This is preferably short-stretch compression material and has section 611 goes on the plantar or bottom aspect of the foot, and section 610 that goes on the dorsal aspect of the foot. Dotted lines form a rectangle 609 on the side, showing where excision of the short-stretch material may allow better stretching on the sides of the garment. It is understood that if three bands are used 603, than similar three bands instead of two might be needed for section 609, so there would be two smaller rectangular shapes instead of one large one. Optional padding may be included on the underside of the section 610, as described in detail above for the dorsal hand embodiments. It is understood that a compression anklet or compression toecaps can be cooperatively or permanently attached to this compression material of FIG. 6F to make a hybrid compression garment for the lower extremity. Y-shaped or polygonal bands are also possible to create proper vector force alignment to provide proper compression.

Figure 6H:
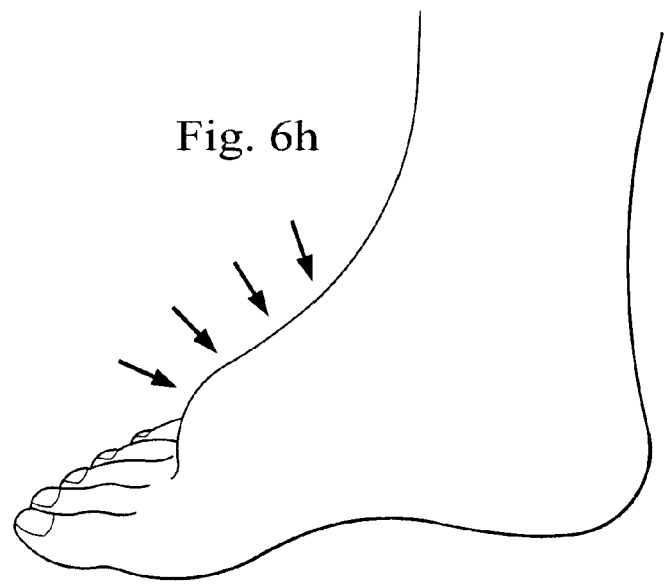

FIG. 6H illustrates a patient with chronic dorsal hump for severe chronic lymphedema. In other cases, the dorsal hump can actually extend over the toe area as an overhanging lobule. Depending on the severity of the hump, it is desirable to compression the hump not only from top to bottom, but also important to compression the hump from the distal top edge of the hump back toward the heel area, with compression vector forces that pull the hump back in and down at the same time in order to effectively reduce it over time. It is understood from this illustration that the number of bands and shape of bands may vary, depending on the size and shape of the dorsal foot hump as needed in order to provide a summation compressive vector force which reduces the dorsal fluid hump/swollen lobule effectively. After application of compression over time, these dorsal humps can shrink and reduce back toward normal size, generally over 6 months to 1 year. In rare cases, decompressed humps may require surgical debulking and removal of excess tissue, but with proper compression these can be corrected. The author is not aware of any products which adequately address and treat these dorsal foot humps other than bandaging, and feels strongly as a medical professional and lymphedema expert that a short-stretch type compression garment disclosed is a significant invention to improve patient care and provide a simpler and more elegant solution to reduce and control swelling, that is easier to apply. Thus the current invention represents a major step forward in improving patient self care and reducing health care costs.

Figure 7:
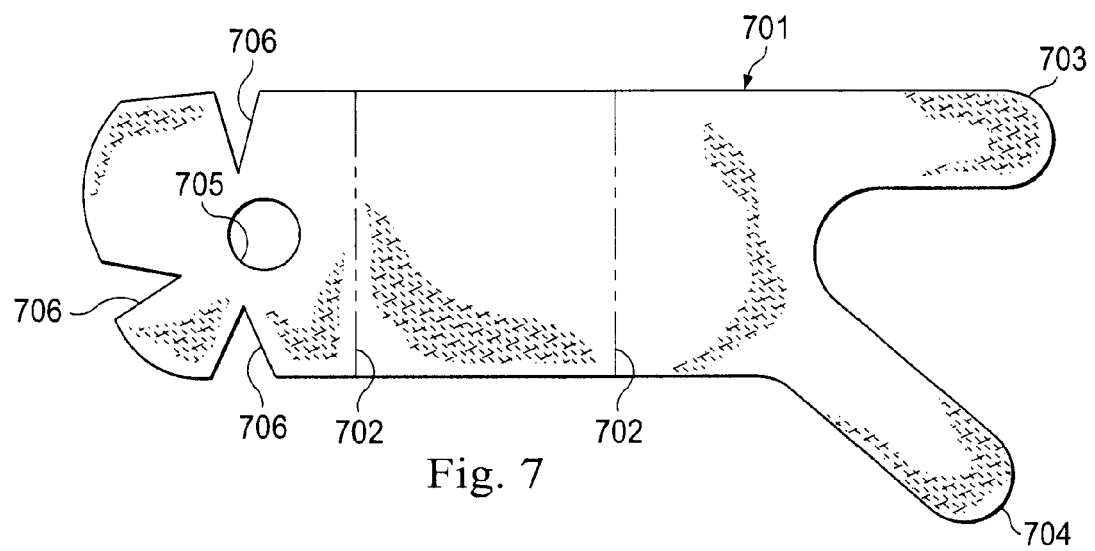
FIG. 7 is an illustration of one embodiment of a compression hand gauntlet.
Figure 8A:
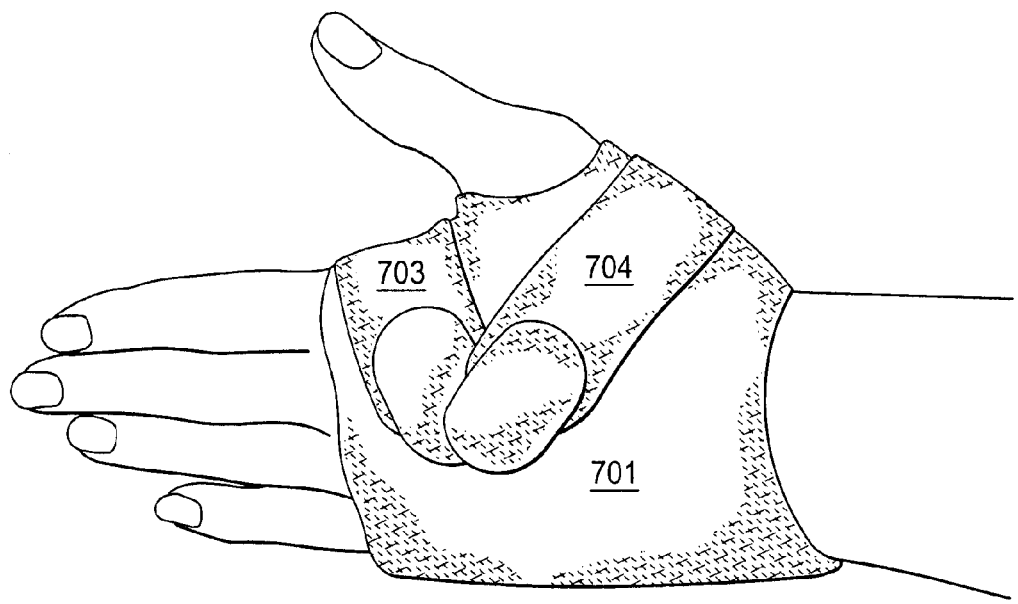
FIGS. 8a and 8b are illustrations of the dorsal hand with a compression gauntlet applied.
Figure 8B:
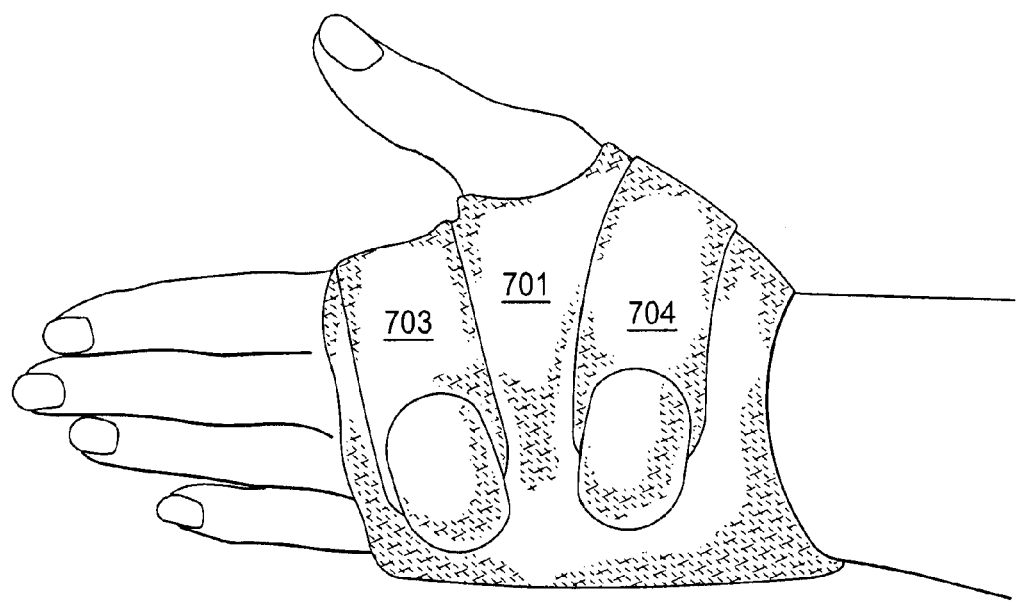

FIG. 7 shows another embodiment of the current invention. The garment 701 has one straight band 703 and one angled band 704. The angle of the band is again chosen to give the proper vector summation forces for maximum comfort and therapeutic compression throughout the range of motion of the wrist while the user is wearing the compression device. It may in turn be combined with a triangular or polygonal hook compatible material (Velcro® or similar brand) to apply even tension over the dorsal hand. 702 shows the borders where optional padding would go, 705 shows the thumb hole, and optional cuts 706 show how to remove material and then sew edges 706 together or otherwise fasten such that the garment closely conforms to the shape of the thenar eminance and palm regions. FIGS. 8a and 8b show the dorsal hand with compression garment 701 applied. Note that the angle of the bands can be altered somewhat in order to provide the best comfort and therapeutic compression to the underlying hand region(s). The garment shown here is somewhat more problematic, however, as it does not provide an even vector force throughout the dorsal part of the hand, which is problematic when the wrist is dorsally extended. This can be at least in part remedied with a triangular shaped or polygonally shaped piece of Velcro® like hook material.

Some embodiments of the garment in FIG. 1, FIG. 7, or FIG. 9 have thumb spica sewn in place with compression material 606 to the thumb digit. This ensures comfort, range of motion, and compression to minimize thumb swelling.

Figure 9A:
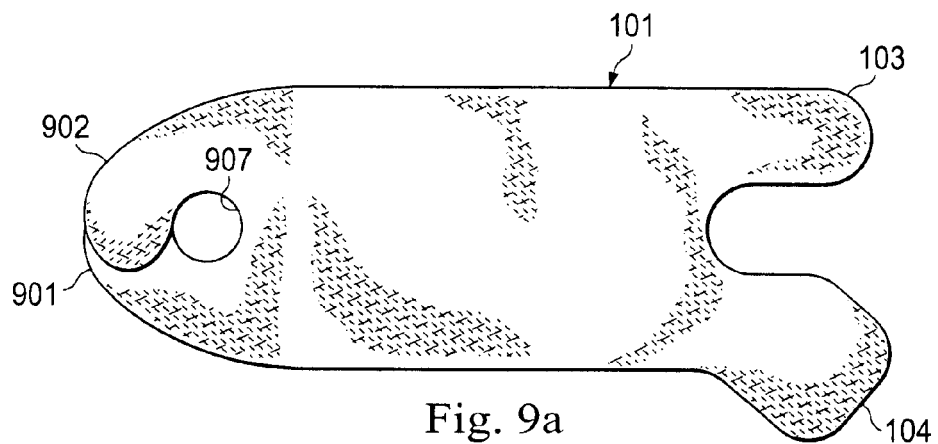
FIGS. 9a and 9b are illustrations of compression devices with thumb bands.

FIG. 9a illustrates an embodiment of the current invention with adjustable thumb hole size. This is achieved with circular shaped bands 901 and 902 which can be trimmed or applied over each other with variability, in order to maximize comfort around the thumb area and better fit different diameter thumbs. Since the garment is applied with compression, there can be pull on the skin at the base of the thumb and hence comfortable fit here is important when garment is to be worn every day for long term use. 901 illustrates the location of the thumb when the garment is donned.

Figure 9B:
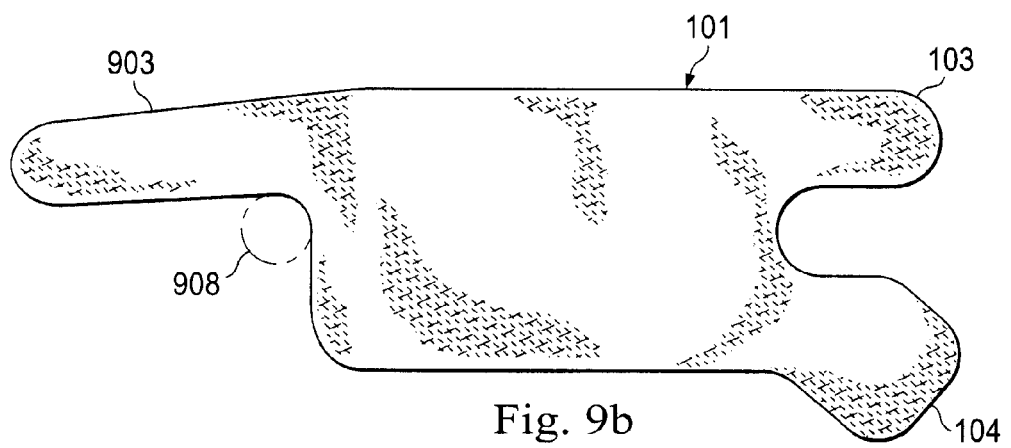

FIG. 9b illustrates another embodiment of a compression garment. In this embodiment, compression band 903 is longer and can wrap around the thumb and reanchor onto itself or the garment material 101, conforming to the thenar eminence area. Velcro® hook material may be sewn on the end of one side of the garment, or may be detachable such that if the garment is constructed with UBL type material laminated together, the garment can be used ambidextrously.

It is understood from the above illustrations and descriptions that other versions are possible, and different concepts of the current invention can be mixed and matched. Furthermore, the garment can also be manufactured as a disposable or semi-reusable short-stretch or nonelastic compression material, designed for clinic and hospital use. One example would be to take short-stretch type Coban® material, which is utilized on the Coban Two Layer compression system, and use thin layer of foam and short-stretch compression Coban type material to make a disposable self-adhesive one time use garment. This provides additional revenue stream for the manufacturer, and may reduce risk of contamination of the garment/bandage, although this is certainly may not be a cost effective or environmentally friendly as a reusable garment on a long term basis.

It is also understood that a two way or four way stretch spacer fabric may be used for compression material 101 or 601 for any of the embodiments, with lamination to a compression fabric or UBL fabric or alone, to make a semireusable garment.

It is also understood that any of the garments described herein can be used with the glove to create a hybrid garment.

Customization

The compression garment 101 and 601 are designed such that these garments can be trimmed as needed with minimum risk of fraying. The trimming may be done along the edges of the garment or the bands, or to expand the thumb hole. Trimming can allow better sizing for a patient of the compression garment and reduce need for inventory. Trim lines can be marked on the garment in order to trim the garment to fit either the right or left hand, or to indicate the size. Trim lines preferably automatically take in the degree of stretch and are spaced appropriately for a garment that is applied at or near end stretch. This was described in prior commonly owned U.S. patent application Ser. No. 12/391,051, filed Feb. 23, 2009, titled "Therapeutic Compression Garments" and in U.S. Provisional Patent Application No. 61/185,129, filed Jun. 26, 2009, titled "Customizable Therapeutic Compression Garment and Method" both which are incorporated herein by reference.

It is understood from above description that a resting compression level is one where compression level is not altered by muscle activation or gravity. Typically, these levels are measured when patient is supine and at rest.

We claim:

1. A hybrid compression device to apply therapeutic compression to a hand of a patient, the device comprising:
    a fabric glove having a palm portion and exhibiting four-way stretch compression;
    a wrap configured to wrap around the palm portion;
    the wrap comprising a first end connected to the fabric glove and a second end opposite the first end; and
    the wrap further comprising a cutout permitting a thumb of the hand to extend through the wrap, the cutout comprising a notch dividing the second end of the wrap into a first band and a second band.

2. The hybrid compression device of claim 1, wherein the wrap comprises short-stretch material exhibiting a user-appreciable end stretch or lock out after an elongation of between 15 and 100 percent.

3. A method of providing therapeutic compression to a hand of a lymphedema patient, the method comprising:
    obtaining a compression device comprising
        a wrap comprising a first cutout positioned proximate one end thereof, a second cutout positioned proximate an opposite end thereof, the second cutout dividing the opposite end of the wrap into a first band and a second band, and
        first and second fasteners respectively attached to the first and second bands;
    selecting a hand of a patient suffering from lymphedema;
    placing a thumb of the hand within the first cutout;
    wrapping the wrap around the hand until the thumb is positioned within the second cutout; and
    securing, by the first and second fasteners, corresponding ends of the first and second bands, respectively, to the wrap.

4. The method of claim 3, wherein the obtaining comprises obtaining the compression device with the wrap comprising short-stretch material exhibiting a user-appreciable end stretch or lock out after an elongation of between 15 and 100 percent.

5. The method of claim 3, further comprising providing, after the securing, therapeutic compression in the range of 15 to 50 mmHg to the hand.

6. The method of claim 3, wherein the obtaining comprises obtaining the compression device with a padding layer on an underside of the wrap.

7. The method of claim 6, wherein the obtaining comprises obtaining the compression device with the padding layer comprising spacer fabric.

8. The method of claim 6, wherein the obtaining comprises obtaining the compression device with the padding layer being selectively removable from the wrap.

9. The method of claim 6, wherein the wrapping comprising positioning the padding layer over a dorsal portion of the hand.

10. The method of claim 3, wherein the wrapping comprising positioning a padding layer over a dorsal portion of the hand.

11. A method of providing therapeutic compression to a hand of a patient suffering from edema, the method comprising:
    obtaining an inside-out reversible compression garment comprising
        a wrap comprising a first cutout positioned proximate one end thereof, a second cutout positioned proximate an opposite end thereof, the second cutout dividing the opposite end of the wrap into a first band and a second band, and
        first and second fasteners respectively attached to the first and second bands;
    selecting a hand of a patient suffering from edema;
    placing a thumb of the hand within the first cutout;
    wrapping the wrap around the hand until the thumb is positioned within the second cutout; and
    securing, by the first and second fasteners, corresponding ends of the first and second bands, respectively, to the wrap.

12. The method of claim 11, further comprising determining, before the placing, which side of the wrap is to be outside based on whether the hand is a right hand or a left hand.

13. The method of claim 12, wherein the obtaining comprises obtaining the inside-out reversible compression garment comprising the wrap having a first side and a second side, opposite the first side, the first and second sides each comprising loop material suitable for engaging hook material of the first and second fasteners.

14. The method of claim 13, further comprising switching, before the securing, the first and second fasteners from the first side to the second side.

15. The method of claim 11, wherein the obtaining comprises obtaining the inside-out compression garment wherein the wrap comprises short-stretch material exhibiting a user-appreciable end stretch or lock out after an elongation of between 15 and 100 percent.

16. The method of claim 11, further comprising providing, after the securing, therapeutic compression in the range of 15 to 50 mmHg to the hand.

\* \* \* \* \*

UNITED STATES PATENT AND TRADEMARK OFFICE
CERTIFICATE OF CORRECTION

PATENT NO. : 8,529,483 B2  
APPLICATION NO. : 12/576899  
DATED : September 10, 2013  
INVENTOR(S) : Wade P. Farrow et al.

Page 1 of 1

It is certified that error appears in the above-identified patent and that said Letters Patent is hereby corrected as shown below:

The list of inventors in item 75 of the title page should include:
        Shmuel Lahav, Petah-Tikva (IL);
        Revital Nowogrod, Ramat-Gan (IL); and
        Rachel Uzan, Petah-Tikva (IL).

Signed and Sealed this  
Tenth Day of March, 2015

Michelle K. Lee  
*Deputy Director of the United States Patent and Trademark Office*